US010835156B2

(12) United States Patent
Hung et al.

(10) Patent No.: US 10,835,156 B2
(45) Date of Patent: Nov. 17, 2020

(54) THERMAL TAGS FOR REAL-TIME ACTIVITY MONITORING AND METHODS FOR FABRICATING THE SAME

(71) Applicant: INTERNATIONAL BUSINESS MACHINES CORPORATION, Armonk, NY (US)

(72) Inventors: Li-Wen Hung, Mahopac, NY (US); Jui-Hsin Lai, White Plains, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 16/425,417

(22) Filed: May 29, 2019

(65) Prior Publication Data

US 2019/0274594 A1 Sep. 12, 2019

Related U.S. Application Data

(63) Continuation of application No. 15/296,115, filed on Oct. 18, 2016, now Pat. No. 10,376,186.

(51) Int. Cl.
*G01K 1/02* (2006.01)
*A61B 5/11* (2006.01)
(Continued)

(52) U.S. Cl.
CPC ............ *A61B 5/1127* (2013.01); *A61B 5/015* (2013.01); *A61B 5/1113* (2013.01);
(Continued)

(58) Field of Classification Search
CPC ........ G01K 17/20; G01K 11/125; G01K 3/00; G01K 3/005; G01K 2213/00; G01K 11/12;
(Continued)

(56) References Cited

U.S. PATENT DOCUMENTS 4,490,053 A * 12/1984 Coston ..................... G01K 3/00
338/214
4,602,159 A * 7/1986 Kasahara .................. G01J 5/44
250/338.1
(Continued)

FOREIGN PATENT DOCUMENTS

CN 201100973 Y 8/2008
CN 101651784 A 2/2010
(Continued)

OTHER PUBLICATIONS

Final Rejection for U.S. Appl. No. 15/205,666 dated Mar. 11, 2019 (18 pages).
(Continued)

*Primary Examiner* — Gail Kaplan Verbitsky
(74) *Attorney, Agent, or Firm* — Tutunjian & Bitetto, P.C.; Kristofer Haggerty

(57) ABSTRACT

A thermal tag for activity monitoring. The thermal tag includes a base layer having a plurality of metal lines to provide a conductive path, and a pattern layer having one or more infrared emitting features positioned over portions of the conductive path, wherein at least one infrared emitting feature couples to the conductive path to emit a predetermined infrared pattern in accordance with nearby activity.

16 Claims, 7 Drawing Sheets

(51) Int. Cl.
*A61B 5/01* (2006.01)
*H01L 33/60* (2010.01)
*H01L 33/62* (2010.01)
*G01K 11/12* (2006.01)
*A61B 90/00* (2016.01)
*H01L 25/075* (2006.01)

(52) U.S. Cl.
CPC ............ *A61B 5/1118* (2013.01); *A61B 5/1128* (2013.01); *H01L 33/60* (2013.01); *H01L 33/62* (2013.01); *A61B 5/1123* (2013.01); *A61B 2090/3979* (2016.02); *A61B 2562/12* (2013.01); *G01K 1/02* (2013.01); *G01K 11/12* (2013.01); *H01L 25/0753* (2013.01); *H01L 2933/0058* (2013.01); *H01L 2933/0066* (2013.01)

(58) Field of Classification Search
CPC ............ G01K 1/02; H01L 2924/12041; G01N 21/0332; A61B 5/1127
USPC ......... 374/121.137, 101, 112, 178, 110, 162; 340/870.17; 257/81, 84, 88; 600/474; 702/135
See application file for complete search history.

(56) References Cited

U.S. PATENT DOCUMENTS

| | | | |
|---|---|---|---|
| 4,733,079 A * | 3/1988 | Adams | G06K 7/12 209/577 |
| 4,998,010 A | 3/1991 | Chandler et al. | |
| 5,054,936 A * | 10/1991 | Fraden | G01J 5/16 257/E27.122 |
| 5,357,095 A | 10/1994 | Weyrauch et al. | |
| 5,414,405 A | 5/1995 | Hogg et al. | |
| 5,585,625 A * | 12/1996 | Spies | G01S 17/026 250/221 |
| 5,678,928 A * | 10/1997 | Agari | B23Q 1/0063 384/45 |
| 5,689,241 A | 11/1997 | Clarke, Sr. et al. | |
| 5,736,723 A | 4/1998 | Clarke et al. | |
| 6,104,295 A | 8/2000 | Gaisser et al. | |
| 7,152,805 B2 | 12/2006 | Walmsley et al. | |
| 7,290,720 B2 | 11/2007 | Walmsley et al. | |
| 7,393,380 B2 | 7/2008 | Smolsky | |
| 8,256,113 B2 * | 9/2012 | Hochstein | H05K 1/0203 29/854 |
| 8,637,897 B2 * | 1/2014 | Kim | H01L 33/08 257/103 |
| 8,659,423 B2 | 2/2014 | Kuris et al. | |
| 8,692,221 B2 | 4/2014 | Ford | |
| 9,060,714 B2 | 6/2015 | Bajcsy et al. | |
| 9,176,990 B2 | 11/2015 | Stuart et al. | |
| 9,291,607 B2 | 3/2016 | Chen et al. | |
| 9,765,934 B2 * | 9/2017 | Rogers | H01L 24/24 |
| 9,823,747 B2 | 11/2017 | Underkoffler et al. | |
| 2004/0119603 A1 * | 6/2004 | Bohlander | B60Q 3/14 340/815.45 |
| 2007/0291473 A1 * | 12/2007 | Traynor | A01K 11/00 362/106 |
| 2008/0138289 A1 | 6/2008 | Goronkin et al. | |
| 2010/0011982 A1 | 1/2010 | Wich | |
| 2010/0189313 A1 | 7/2010 | Prokoski | |
| 2011/0001605 A1 | 1/2011 | Kiani et al. | |
| 2011/0105854 A1 | 5/2011 | Kiani et al. | |
| 2012/0191164 A1 * | 7/2012 | Gander | H05B 3/12 607/96 |
| 2014/0148733 A1 * | 5/2014 | Stone | G16H 50/30 600/595 |
| 2015/0002023 A1 * | 1/2015 | Imangholi | G01K 7/00 315/129 |
| 2016/0065909 A1 | 3/2016 | Derenne et al. | |
| 2018/0011982 A1 | 1/2018 | Hung et al. | |
| 2019/0206671 A1 * | 7/2019 | Zissing | H05B 3/0038 |

FOREIGN PATENT DOCUMENTS

| | | |
|---|---|---|
| CN | 102483877 A | 5/2012 |
| CN | 103617997 A | 3/2014 |
| CN | 105308657 A | 2/2016 |
| CN | 105590901 U | 5/2016 |
| JP | H0815007 A | 1/1996 |
| KR | 20060089335 A | 8/2006 |

OTHER PUBLICATIONS

Chinese Office Action from related case 201780064193.9, dated Jul. 30, 2020, 10 pages.

* cited by examiner

THERMAL TAGS FOR REAL-TIME ACTIVITY MONITORING AND METHODS FOR FABRICATING THE SAME

BACKGROUND

Technical Field

The present invention generally relates to activity monitoring and, in particular, to the thermal tags to track activity with minimal privacy concerns and methods for fabricating the same.

Description of the Related Art

There is a significant need to monitor patient activity, for example during convalescence or for elder care in the home. In such cases, a doctor may need to know how treatments, or the symptoms of a disease, are progressing despite the patient being at a remote location. However, conventional video monitoring poses significant privacy concerns. In particular, while a conventional color camera provides the ability to remotely monitor a patient's activity, such cameras will also capture information that may include, for example, images displayed on a computer or television screen or the writing on a sheet of paper. As a result, patients may be reluctant to allow such monitoring, despite the definite benefits that the monitoring might otherwise provide.

SUMMARY

A thermal tag for activity monitoring, the thermal tag includes a base layer having a plurality of metal lines to provide a conductive path, and a pattern layer having one or more infrared emitting features positioned over portions of the conductive path, wherein at least one infrared emitting feature couples to the conductive path to emit a predetermined infrared pattern in accordance with nearby activity.

A thermal tag for activity monitoring, the thermal tag includes a base layer having a plurality of metal lines to provide a conductive path, wherein the plurality of metal lines form a metal grid to emit infrared light, and a pattern layer having one or more infrared reflective features positioned over portions of the conductive path, wherein at least one infrared reflective feature blocks portions of the infrared light to provide a predetermined infrared pattern in accordance with nearby activity.

A method for fabricating a thermal tag for activity monitoring includes forming a plurality of metal lines to provide a conductive path on a base layer, forming one or more infrared emitting features positioned over portions of the conductive path on a pattern layer, and coupling the base layer to the emitting layer, wherein at least one infrared emitting feature couples to the conductive path to emit a predetermined infrared pattern in accordance with nearby activity.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein.

DETAILED DESCRIPTION

Embodiments of the present invention provide thermal tags detectable by infrared cameras for activity monitoring and methods for fabricating the same. Infrared imaging detects electromagnetic radiation in the infrared band, which is invisible to the naked eye and which is commonly created by warm objects (such as, e.g., the human body). Infrared light can also be generated by artificial means. As such, the present embodiments describe thermal tags to track motion of the patient using an infrared camera and, in addition, tracks the patient's interactions with objects in the environment through the use of infrared emitting tags attached to objects of interest.

In some embodiments, the thermal tags described herein include a plurality of layers, some of which may be disposable. The thermal tags can include a flexible substrate having electrically conductive, thermally conductive, and/or reflective material to provide a distinct thermal pattern detectable by thermal imaging techniques. In some embodiments, the thermal tags include infrared light emitting diodes (LEDs) which emit infrared light in a predetermined pattern. Accordingly, the thermal tags are detectable using infrared imaging, thereby avoiding privacy-invading capabilities of conventional video monitoring and providing a low cost object tracking mechanism. In some embodiments, one or more of the layers of the thermal tags may be removable and/or disposable such that the thermal tags are reconfigurable and provide varying infrared emitting patterns.

Figure 1:
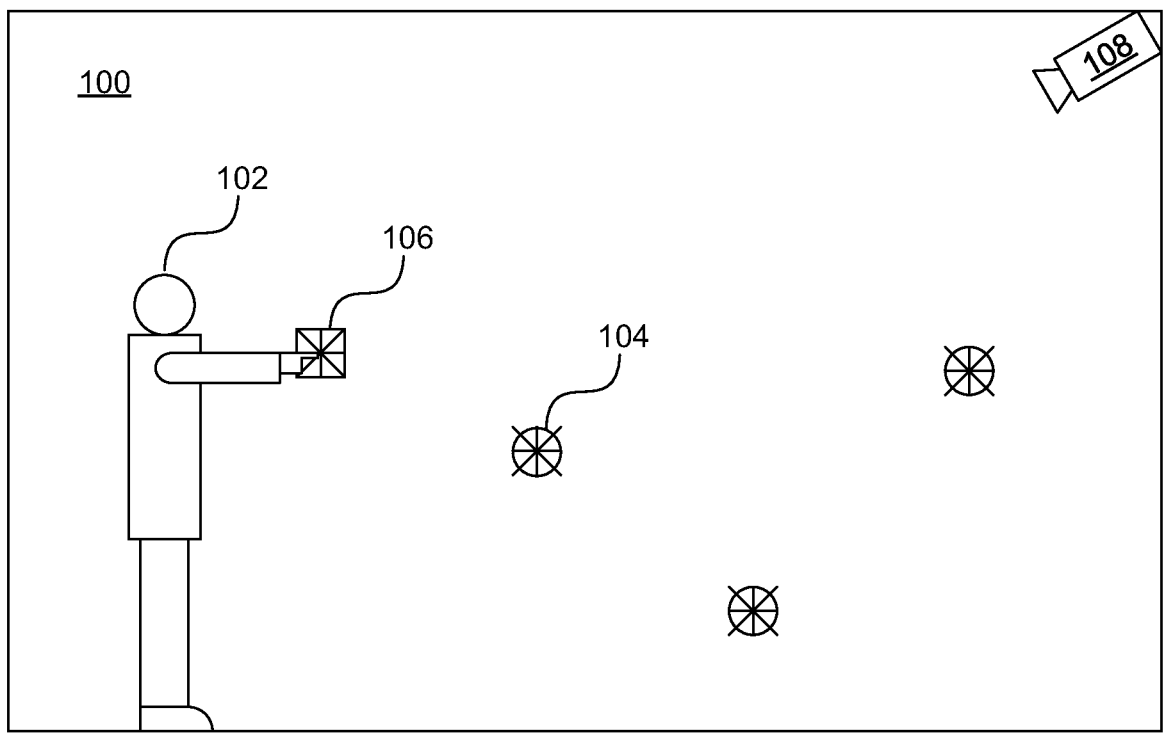
FIG. 1 is a diagram of a monitored environment in accordance with an embodiment of the present invention.

Referring now to the drawings in which like numerals represent the same or similar elements and initially to FIG. 1, an exemplary monitoring environment 100 is shown. The environment 100 includes at least one user 102. The user 102 may be, for example, a person who is injured or sick, an elderly person, or any person who would benefit from activity monitoring. In addition, a number of objects 104 are present in the environment 100 that include thermal tags. The objects 104 emit a continuous or pulsed infrared signal via the thermal tags. In an embodiment using a pulsed infrared signal, each object 104 may be assigned a unique pattern that distinguishes the object from other objects.

An infrared monitoring device 108 captures infrared information from the environment. It should be noted that multiple monitoring devices 108 can be used in a single environment to cover all of the potential angles of view. The monitoring device 108 may take still images or may alternatively capture video of the infrared emissions of the environment 100. It should be understood that the present principles may be applied to other types of imaging device, but infrared is particularly contemplated because human bodies inherently emit detectable levels of infrared radiation. Limiting the monitoring device 108 strictly to infrared is not needed for the functioning of the present embodiments, but serves to prevent potential privacy infringement that might arise from recording visible light information.

The user 102 emits infrared radiation by virtue of body heat, while the objects 104 emit infrared radiation from their respective thermal tags. The infrared light is captured by the monitoring device 108 and can be used to show the user's activities in the environment 100. For example, if the user 102 picks up an object 106 (e.g., a cane), the monitoring device 108 will capture that event. However, being limited to infrared radiation, the monitoring device 108 will not detect untagged objects unless they differ in temperature from the ambient temperature. As a result, the monitoring device 108 is not able to resolve the details of printed subject matter or the display of screens, as these surfaces generally present a uniform temperature that does not depend on the content.

The information captured by the monitoring device 108 can be of significant use in medical treatment. It may be of interest, for example, how often a patient suffering from Parkinson's disease uses a cane. A thermal tag may therefore be attached to the cane, such that instances where the user 102 is carrying the cane may be recorded and logged.

Figure 2:
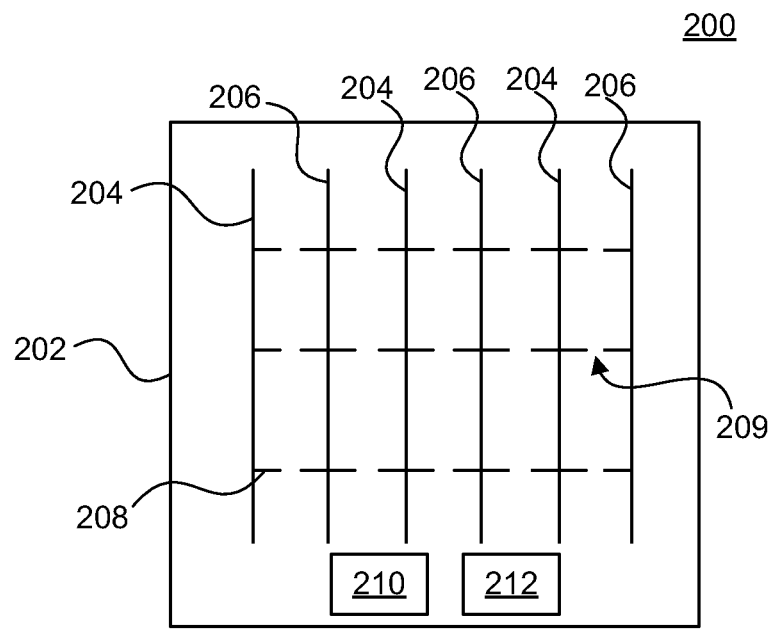
FIG. 2 is a top view showing an infrared-emitting tag in accordance with an embodiment of the present invention.

Referring now to FIG. 2, with continued reference to FIG. 1, a top view of a base layer 202 for an exemplary infrared tag 200 is shown. The tag 200 includes a plurality of layers. For example, the tag 200 can include at least two layers, wherein the two layers includes a base layer 202 and a pattern layer (not shown), as will be described in further detail below. The plurality of layers may be directly coupled such that the layers are in direct contact, or alternatively may be indirectly coupled, as will be described in detail below.

In some embodiments, the base layer 202 includes a flexible substrate, such as one or more dielectric materials (e.g., silicone, Kapton tape, etc.), however other materials are readily contemplated. The flexible substrate allows the thermal tag 200 to conform to object shapes easily. The base layer 202 includes a plurality of metal lines 204, 206 that form a conductive path. For example, the conductive path includes metal lines 204, 206, such as wide metal traces having low resistance. The wide metal traces can include, for example, direct current (DC) bias lines 204 and ground (GND) lines 206 alternatively arranged across the base layer 202. In some embodiments, portions of the lines 204, 206 are completely embedded within the material of the base layer 202, while other portions of the lines 204, 206 connecting to one or more infrared emitting features remains exposed, as will be described in further detail below.

As shown in FIG. 2, the metal lines 204, 206 are spaced apart within the material of the base layer 202. For example, adjacent DC bias lines 204 and GND lines 206 are separated. In some embodiments, the metal lines 204, 206 include one or more metal trace points 208 positioned along the one or more metal lines 204, 206. The metal trace points 208 may correspond to and/or may be positioned with respect to metal trace points 208 on adjacent metal lines 204, 206. In some embodiments, the metal trace points 208 remain exposed on the surface of base layer 202 while the metal lines 204, 206 are embedded within the base layer 202 and therefore are not exposed on the surface of base layer 202.

In an embodiment, the metal trace points 208 do not extend fully between adjacent metal lines 204, 206. As shown in FIG. 2, the metal trace points 208, and therefore adjacent metal lines 204, 206, are separated by a gap 209. The gap 209 prevents current from arbitrarily passing between the adjacent metal lines 204, 206. When current passes along the conductive path and between metal lines 204, 206, as will be described in further detail below, heat is generated and infrared light is emitted.

The base layer 202 may include a power source 210 and a pulse generator 212. The power source 210 may be any appropriate device for storing or generating electrical power. In one example, the power source 210 may be a simple battery (e.g., a coin cell or other small battery). In another example, the power source 210 may convert power from, e.g., light or motion into electrical energy that may then be stored in a battery or capacitor. The power source 210 supplies electrical power to the conductive path (e.g., metal lines 204, 206).

In some embodiments, the power source 210 and metal lines 204, 206 are connected via a pulse generator 212. The pulse generator 212 allows current to pass from the power source 210 to the line 204, 206. In some embodiments, the pulse generator 212 may include a simple circuit having a least one switch that generates a pulse current by connecting and disconnecting the power source 210 to lines 204, 206 periodically. The current is generated along the conductive path (e.g., metal lines 204, 206), thereby generating heat and emitting infrared light from infrared emitting features, as will be described below. It should be noted that lines 204, 206 are wider than infrared emitting features 304 in FIG. 3 such that with the same current, most of the current/heat is generated at locations corresponding to the infrared light emitting features 304. Thus, heat generated at lines 204, 206 is minimized.

Figure 3:
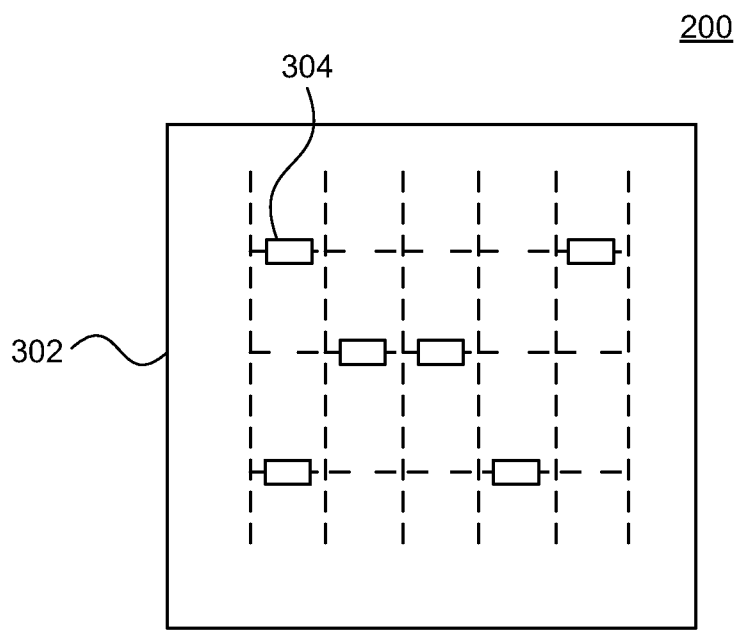
FIG. 3 is a top view showing an infrared-emitting tag in accordance with an embodiment of the present invention.

Now referring to FIG. 3, with continued reference to FIG. 2, a top view of a pattern layer 302 for an exemplary infrared tag 200 is shown. The tag 200 include a pattern layer 302 which may be coupled directly and/or indirectly to the base layer 202. In some embodiments, the base layer 202 and the pattern layer 302 can be coupled by thermally activated glue. As both the base layer 202 and the pattern layer 302 are flexible substrates, they can be placed under a roller with thermally activated glue applied to either the base layer 202 or the pattern layer 302 surface. It should be noted that such placement of the glue should be avoided on the metal trace points 208. A heated roller rolls from one edge to the other of layers 202, 302 so as to couple the layers 202, 302 together. To detach the layers 202, 302, heat can be applied again to peel the layers 202, 302 apart. For example, the pattern layer 302 may be coupled to the base layer 202 by an adhesive layer, adhesive strip, and/or magnetic forces (not shown).

In some embodiments, the pattern layer 302 includes a plurality of infrared emitting features 304 positioned along the conductive path in a distinct pattern. For example, the infrared emitting features 304 may include electrically high resistive material. The infrared emitting features 304 can include a printed thin metal and/or high resistive material, such as conductive carbon ink, aluminum particles mixed in printable polymer paste, laminated thin aluminum foil, printable conductive polymer, etc. In some embodiments, the infrared emitting features 304 include light emitting diodes (LEDs).

As shown in FIG. 3, the infrared emitting features 304 are selectively positioned over portion of the conductive path such that when the infrared emitting features 304 are coupled to the conductive path, the infrared emitting features 304 electrically connect the metal lines 204, 206 and emit infrared light in a predetermined infrared pattern. Each thermal tag 200, therefore, may emit distinct infrared patterns based on positioning of the infrared emitting features 304. Accordingly, interchangeable pattern layers 302 having different layouts of infrared emitting features 304 may be employed using the same base layer 202.

In some embodiments, the amount of and position of the infrared emitting features 304 (e.g., rows, columns) may provide a predetermined infrared pattern representative of a code. The code may be indicative of the specific tagged object 104 (e.g., a cane, a medicine bottle, etc.) which the tag 200 is attached to. The infrared emitting features 304 are positioned within the gap between metal lines 204, 206 (shown as dotted lines) and metal trace points 208 (shown as dotted lines) such that respective metal trace points 208 and metal lines 204, 206 are electrically connected via the infrared emitting features 304. Accordingly, current may pass through lines 204, 206 along the conductive path and infrared emitting features 304, thereby emitting a predetermined infrared pattern (e.g., heat) from the infrared emitting features 304.

In an embodiment, the predetermined infrared pattern is representative of a binary code, wherein zero (e.g., "0") represents an absence of infrared light (e.g., no infrared emitting feature 304) and one (e.g., "1") represents a presence of infrared light (e.g., an infrared emitting feature 304). The infrared pattern and/or binary code may be employed as identification to identify the tagged object 104. For example, a predetermined binary code associated with a tagged object 104 may be stored in a storage device (e.g., memory, database, etc.). When the monitoring device 108 detects the unique infrared pattern, the identity of the tagged object 104 may also be determined.

As shown in FIG. 3, tag 200 is shown having a total of six infrared emitting features 304, wherein each infrared emitting feature 304 corresponds to a one of the binary code and each blank spot having no infrared emitting feature 304 corresponds to a zero of the binary code. For illustrative purposes, the pattern layer 302 may form a binary code of "10001_01100_10010" corresponding to infrared emitting features 304 in their respective position. Specifically, the first row may include infrared emitting features 304 in first and fifth columns, the second row may include infrared emitting features 304 in second and third columns, and the third row may include infrared emitting features 304 in first and fourth columns. The binary codes may be stored in a database and may be used to identify the particular tagged object 104. Accordingly, when the monitoring device 108 and/or activity monitoring system detects the infrared pattern emitted by infrared emitting features 304, the monitoring device 108 and/or activity monitoring system may further determine which object the user 102 is interacting with.

In some embodiments, the tag 200 may be reconfigurable by replacing/removing different pattern layers 302 from the base layer 202. Accordingly, the pattern layer 302 may be a "disposable" layer and/or a "replaceable" layer. For example, different pattern layers 302 may have different infrared emitting features 304 which emit different infrared patterns when current is generated within the conductive path. When the varying pattern layers 302 are coupled/connected to the base layer 202, the infrared emitting features 304 generate a unique infrared pattern. A first infrared pattern emitted from a first pattern layer 302 may identify a cane while a second infrared pattern emitted from a second pattern layer 302 may identify a medicine bottle. Accordingly, a user need only couple the base layer 202 with the first pattern layer 302 to track the user's interactions with the cane. Because the base layer 202 provides a conductive path (e.g., a heating source), the base layer 202 may be reused with different pattern layers 302 thereby "reconfiguring" each thermal tag 200.

The infrared emitting features 304 may be disposed (e.g., printed) on or within the pattern layer 302 such that the infrared emitting features 304 are aligned with the conductive path along a predetermined pattern. The infrared emitting features 304 provide a connection between the metal lines 204, 206 (shown as dotted lines) to complete the circuit. For example, the infrared emitting features 304 electrically connect lines 204 and lines 206 when current is applied to the lines 204, 206. When current runs through the infrared emitting features 304, the infrared emitting features 304 generate heat and emit infrared light which may be detected by monitoring device 108 and/or an activity monitoring system.

The layout and/or pattern of the infrared emitting features 304 may be made unique to each infrared tag 200, such that a monitoring device 108 can recognize the emitted infrared pattern and thereby identify the object 104 to which the infrared tag 200 is attached. The infrared tags 200 may be attached with a known orientation and location on each object 104 of interest in the environment 100. In some embodiments, the orientation of the tag 200 is encoded in the infrared pattern emitted by the infrared emitting elements 304. Based on the images captured by the monitoring device 108, which show only the contour of the user's body 102 and the infrared patterns being emitted by the tags 200, images of the user's walking patterns and interactions with the objects 104 can be monitored, tracked and/or reconstructed.

Figure 4:
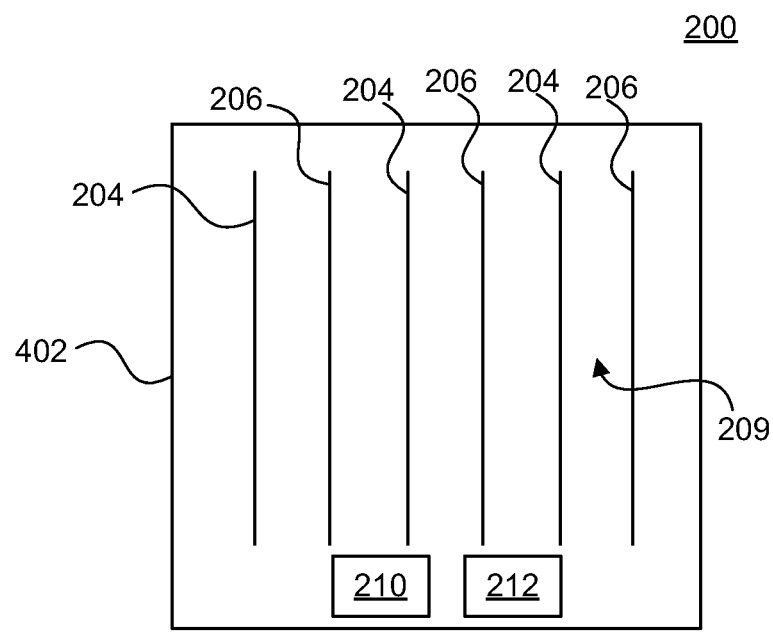
FIG. 4 is a top view showing an infrared-emitting tag in accordance with an embodiment of the present invention.

Now referring to FIG. 4, a top view of base layer 402 for an exemplary infrared tag 200 is shown. As described above, the base layer 402 may include a plurality of metal lines 204, 206 alternatingly arranged across the base layer 402. The metal lines 204, 206 are separated by a gap 209. In addition, the base layer 402 includes a power source 210 and a pulse generator 212, as described above. However, metal trace points 208 are noticeably absent.

Figure 5:
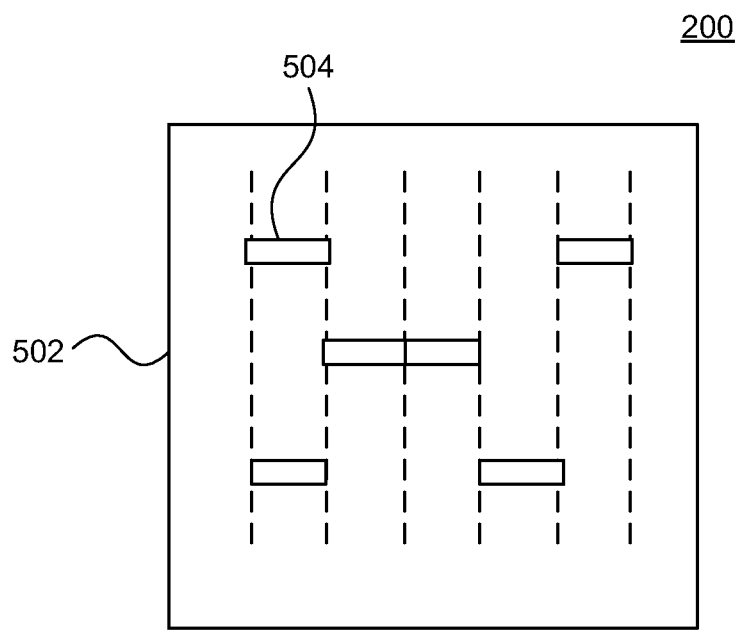
FIG. 5 is a top view showing an infrared-emitting tag in accordance with an embodiment of the present invention.

Referring now to FIG. 5, a top view of pattern layer 502 for the exemplary infrared tag 200 is shown. The metal lines 204, 206 of base layer 402 are shown as dotted lines. In an embodiment, the pattern layer 502 includes one or more infrared emitting features 504. The infrared emitting features 504 include electrically conducting material and/or thermally conducting material. In some embodiments, the infrared emitting features 504 include light emitting diodes (LEDs). As shown in FIG. 5, the one or more infrared emitting features 504 extend the gap 209 to electrically connect adjacent lines 204 with lines 206.

Figure 6:
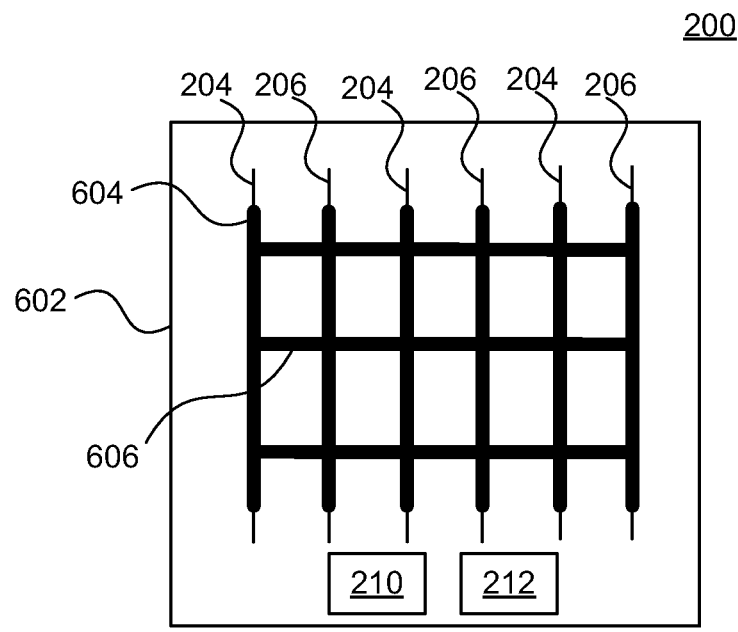
FIG. 6 is a top view showing an infrared-emitting tag in accordance with an embodiment of the present invention.

Now referring to FIG. 6, a top view of a base layer 602 for an exemplary infrared tag 200 is shown. The base layer 602 includes one or more materials including, but not limited to, a dielectric material, silicone, Kapton tape, etc. As described above, the base layer 602 includes a plurality of metal lines 204, 206. In some embodiments, the metal lines 204, 206 include narrowing metal traces at target points to provide heat point sources 606. The heat point sources 606 are directly coupled to metals lines 204, 206. The metal lines 204, 206 are thick and/or wide metal lines of more conductive material and heat point sources 606 are thin, narrow lines of less conductive material. Thus, the resistance of heat point sources 606 is much larger than the resistance of either lines 204 or lines 206. When connected to the power source 210 (e.g., battery), heat is generated mostly at heat point sources 606, thereby providing a 'point' heat source. Thus, heat source points 606 generate more heat than surrounding areas on the base layer 602 due to increased resistance. Such heat point sources 606 may include, for example, a metal connection that electrically connects adjacent metal lines 204, 206.

Portions of the metal lines 204, 206 are encapsulated and/or covered in a thin dielectric material 604. The thin dielectric material 604 prevents DC current flowing to the infrared emitting features 704 of FIG. 7, however the thin dielectric material 604 does not prevent heat to pass from base layer 602 to infrared emitting features 704. As shown in FIG. 6, heat point sources 606 are also covered with the thin dielectric material. In some embodiments, the metal lines 204, 206 are physically and/or electrically connected via heat point sources 606. It should be noted that the dielectric material 604 may be strategically placed over corresponding locations of the lines 204, 206 and heat point sources 606. Alternatively, the dielectric material 604 may include a layer that expands the surface of the base layer 602. The power source 210 supplies power to metal lines 204, 206 to generate heat at heat point sources 606 which emit infrared light.

Figure 7:
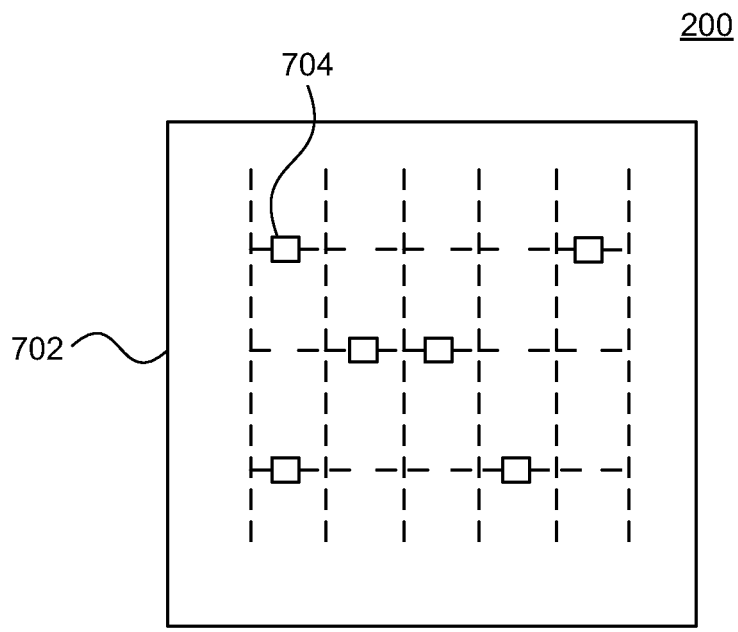
FIG. 7 is a top view showing an infrared-emitting tag in accordance with an embodiment of the present invention.

Referring to FIG. 7, with continued reference to FIG. 6, a pattern layer 702 of tag 200 includes infrared emitting features 704. While the infrared emitting features 704 are shown as square-shaped, other shapes are readily contemplated. The infrared emitting features 704 include thermal conductive patches having a heat spreading element such that when current is applied to the conductive path, and thus heat point sources 606, the heat spreading element of infrared emitting features 704 dissipates the heat generated at such locations.

It should be noted that infrared light is also emitted at heat point sources 606 that are not coupled to infrared emitting features 704. However, the heat spreading element of infrared emitting features 704 causes the emitted infrared light at such locations to be less concentrated. On the other hand, the infrared light emitted at heat point sources 606 not coupled to infrared emitting features 704 will be more concentrated. Accordingly, the infrared light emitted from tag 200 will appear to have a distinguishable infrared pattern where the heat point sources 606 generate smaller concentrated areas of infrared light, and the infrared emitting features 704 having a heat spreading element generates larger, less concentrated areas of infrared light. Thus, the infrared emitting features 704 emits infrared light having a distinct temperature gradient within the infrared pattern.

The infrared emitting features 704 can include a printed thermal conducting material, such as carbon and/or silver paste, however other materials are readily contemplated. One or more of the infrared emitting features 704 are positioned over respective heated point sources 606 (shown as dotted lines) such that the infrared emitting features 504 emit infrared light having less concentration than heat point sources 606 when current is applied to the conductive path. Because the infrared emitting features 704 may be printed, it is easy to generate new patterns (e.g., positions where infrared emitting features 704 are located) and/or codes to tag new objects. When a printed thermal conducting material is employed, the infrared emitting features 704 may appear more homogenous in temperature gradient within the infrared pattern when current is applied to the conductive path.

According, the present invention provides thermal tags 200 which are easily recognizable in various environments. For example, assume the thermal tag 200 is located in environment 100 next to something hot (e.g., a radiator). Both the radiator and the thermal tag 200 emit infrared light, which is detected by a thermal sensor (e.g., monitoring device 108). By providing infrared emitting features 704 having a heat spreading element, the monitoring device 108 can distinguish between the radiator and the thermal tag 200, since thermal tag 200 emits infrared light in a distinguishable pattern having higher and lower concentration points.

Figure 8:
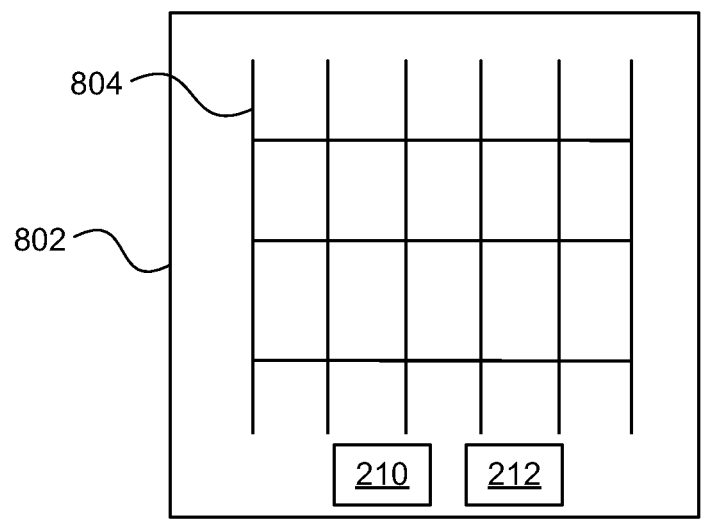
FIG. 8 is a top view showing an infrared-emitting tag in accordance with an embodiment of the present invention.

Referring now to FIG. 8, an embodiment of the base layer 802 of the thermal tag 200 is illustratively depicted. In some embodiments, the base layer 802 includes a plurality of metal lines that form a metal grid 804 (e.g., a conductive path). For example, the plurality of metal lines may include vertical metal lines and horizontal metal lines, wherein adjacent metal lines are connected to form a grid. When the power source 210 provides current to the metal grid 804, the metal grid 804 generates a homogeneous heating profile across the base layer 802, thereby emitting infrared light.

Figure 9:
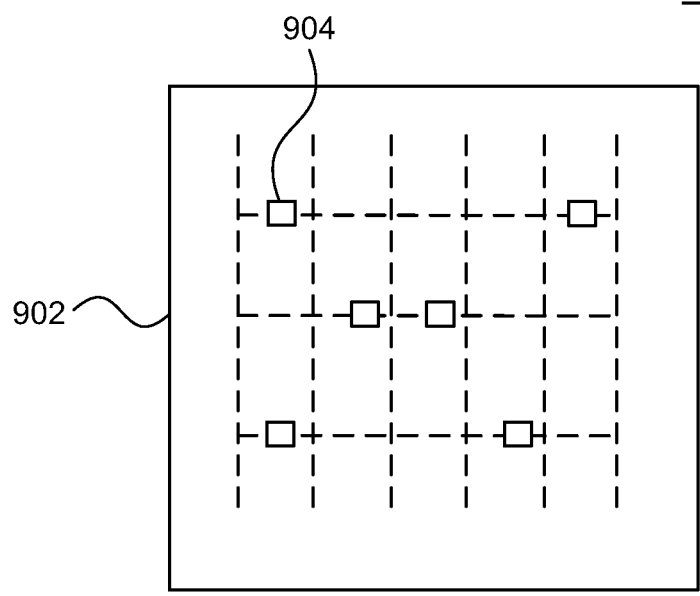
FIG. 9 is a top view showing an infrared-emitting tag in accordance with an embodiment of the present invention.

Now referring to FIG. 9, with continued reference to FIG. 8, the pattern layer 902 includes one or more infrared reflective features 904 positioned over portions of the conductive path (shown as dotted lines). For example, the infrared reflective features 904 are positioned in target areas over the metal grid 804. The infrared reflective features 904 may be printed on the pattern layer 802 and include infrared reflective material, such as aluminum, acrylic, etc. The pattern layer 902 may be coupled to the base layer 802 such that an air gap is present between the pattern layer 902 and the base layer 802.

As described above, a uniform heat profile is formed on the base layer 802 which radiates heat when current is applied to the metal grid 804. Accordingly, the base layer 802 emits infrared light from the metal grid 804. The infrared reflective features 904 block the emitted infrared light from base layer 802 to provide a predetermined infrared pattern unique to each thermal tag 200. For example, the reflective features 904 prevents the monitoring device 108 from detecting infrared light at positions where the reflective features 904 are present. The infrared reflective features 904 reflect and/or block the radiated heat generated by the base layer 802, thereby generating a temperature distribution pattern across the tag 200.

Because the reflective features 904 block infrared light generated at such locations, portions of the thermal tag 200 that include the reflective features 904 may appear colder than other portions of the thermal tag 200 which do not have reflective features 904. Accordingly, the monitoring device 108 can detect the emitted infrared pattern having a temperature distribution pattern to identify the tagged object 104.

Figure 10:
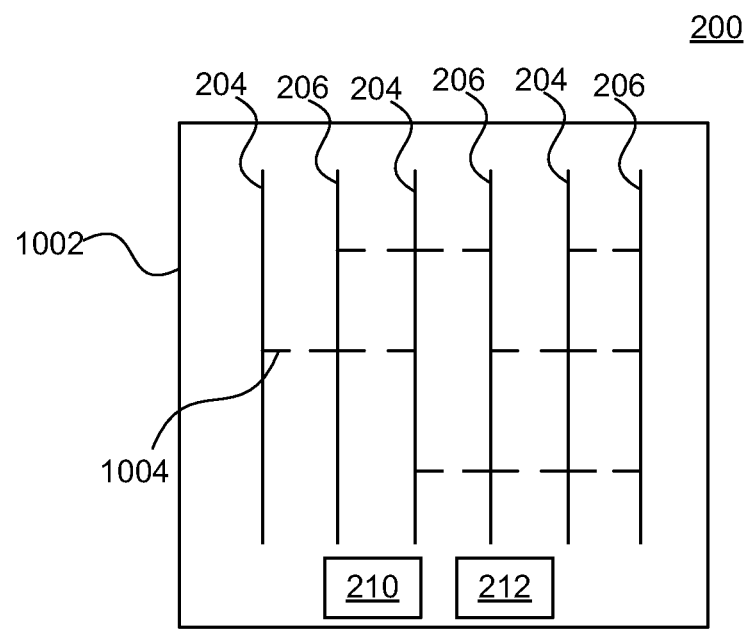
FIG. 10 is a top view showing an infrared-emitting tag in accordance with an embodiment of the present invention.

Referring now to FIG. 10, a top view of a base layer 1002 for an exemplary infrared tag 200 is shown. The base layer 1002 includes a plurality of the metal lines 204, 206 forming a conductive path. The metal lines 204, 206, which may include DC bias lines 204 and GND lines 206, are alternatingly arranged and spaced apart across the base layer 1002 such that the metal lines 204, 206 are separated. The metal lines 204, 206 include one or more metal trace points 1004. The metal trace points 1004 are selectively positioned in a predetermined pattern along the conductive path. As shown in FIG. 10, the metal trace points 1004 extend partially between the metal lines 204, 206 such that the metal lines 204, 206 are separated by a gap. The metal trace points 1004 form a unique pattern specific to the thermal tag 200 and/or tagged object 104. For example, when infrared emitting features 1104 of FIG. 11, such as infrared light emitting diodes (LEDs), are positioned over the metal trace points 1004 (e.g., within the gap), only those LEDs will emit infrared light in a predetermined infrared pattern. Accordingly, the position of the metal trace points 1004 form the unique infrared pattern for the thermal tag 200.

The metal trace points 1004 correspond to a position associated with an infrared light emitting diode (LED). Accordingly, when a current is passed through the metal lines (e.g., from line 204 to line 206) and across metal trace points 1004, select LEDs emit infrared light. The base layer 1002 may include a power source 210 to supply a current along metal lines 204, 206, thereby emitting infrared light from the infrared light emitting diodes (LEDs) coupled to the metal trace points 1004. In an embodiment, the base layer 1002 may be disposable while the pattern layer 1102 of FIG. 11, as described below, may be reused.

Figure 11:
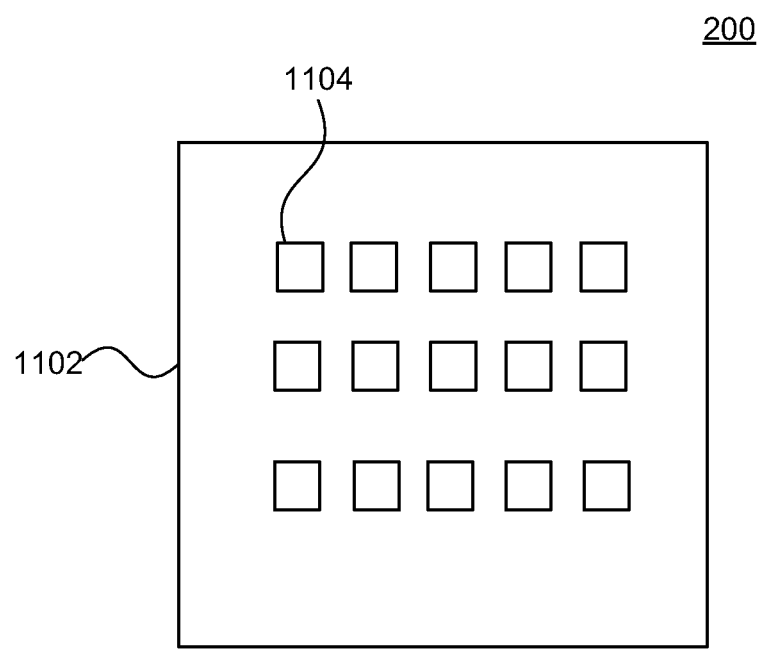
FIG. 11 is a top view showing an infrared-emitting tag in accordance with an embodiment of the present invention.

Now referring to FIG. 11, with continued reference to FIG. 10, an exemplary pattern layer 1102 for thermal tag 200 is shown. The pattern layer 1102 includes an array infrared emitting features 904, such as infrared light emitting diodes (LEDs). An infrared light emitting diode (LED) emits an infrared signal when a current passes through it. When a current passes through the metal trace points 1004, a portion of the infrared emitting features 1104 from the array connect metal trace points 1004 of adjacent metal lines 204, 206. Accordingly, only a portion of the infrared emitting features 904 emit infrared light thereby providing a unique predetermined infrared pattern.

The predetermined infrared pattern may be representative of a code corresponding to a particular tagged object 104. The LEDs 1104 that do not connect/correspond to a metal trace point 1004 do not emit infrared light. Thus, the thermal tag 200 provides a unique infrared pattern emitted from the LEDs 1104. The position of the metal trace points 1004 and/or predetermined infrared pattern may be stored for each infrared tag 200 for tag recognition.

Figure 12:
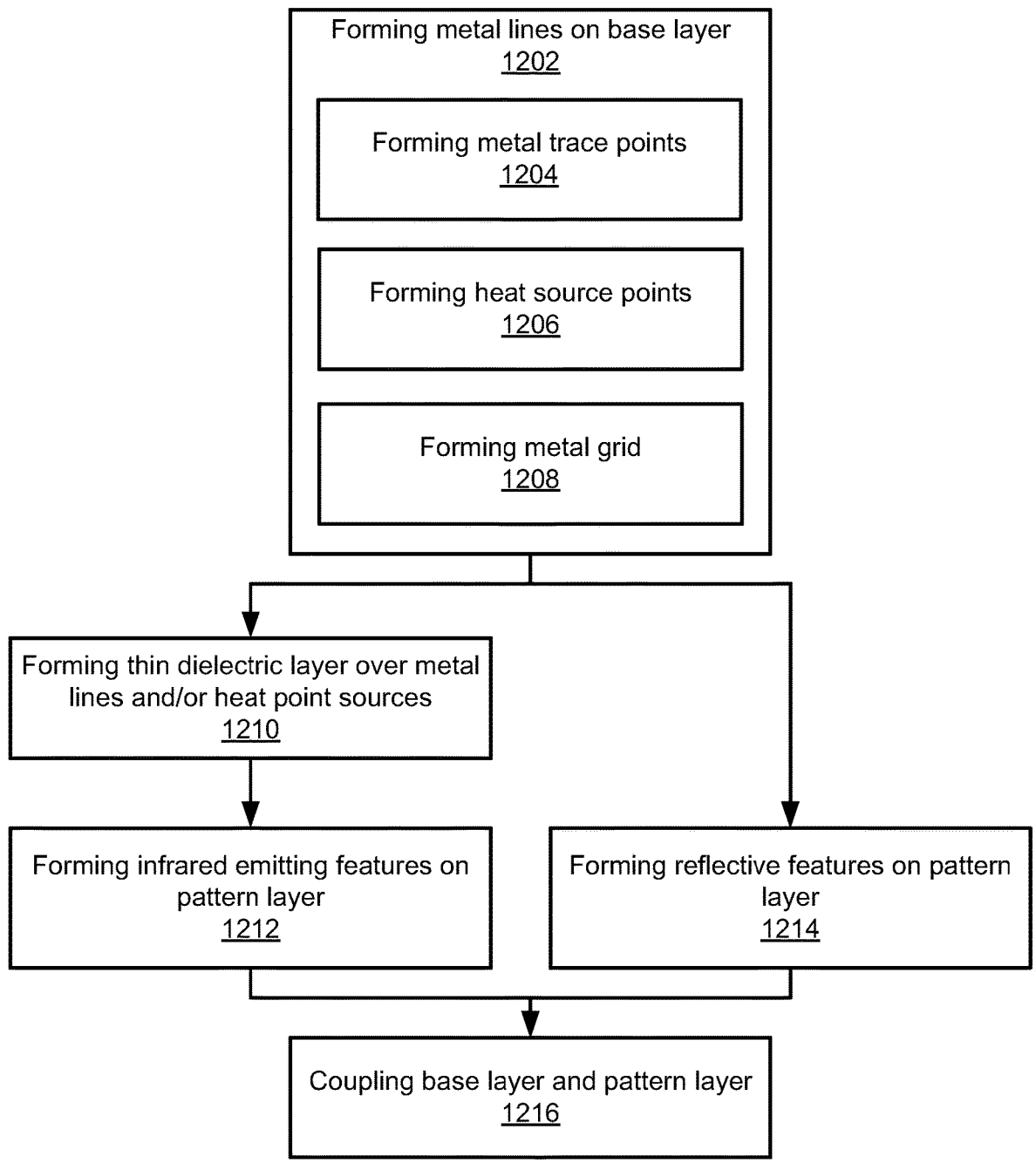
FIG. 12 is a block/flow diagram showing a system/method for fabricating a thermal tag for activity monitoring in accordance with an embodiment of the present invention.

Referring now to FIG. 12, with continued reference to FIGS. 1-11, a method 1200 for fabricating a thermal tag 200 for activity monitoring is shown. Block 1202 forms metal lines 204, 206 on a base layer. The metal lines 204, 206 provide a conductive path. In some embodiments, forming metal lines 204, 206 includes forming one or more metal trace points along the metal lines 204, 206 and/or positioning the metal trace points in a predetermined pattern, as shown in block 1204. For example, the metal trace points may be printed in a predetermined pattern. The metal trace points may form a gap between adjacent metal lines 204, 206. In an embodiment, forming metal lines 204, 206 includes forming heat source points to connect adjacent metal lines 204, 206, as shown in block 1206. In some embodiments, forming metal lines 204, 206 includes forming a metal grid from the metal lines 204, 206 to provide a uniform heat gradient across the base layer, as shown in block 1208.

In block 1210, the method 1200 includes forming a thin dielectric layer over at least portions of the metal lines 204, 206 and/or heat point sources 606 on or within the base layer. The thin dielectric material prevents DC current flowing to the infrared emitting features, however the thin dielectric material does not prevent heat to pass from base layer to infrared emitting features.

Block 1212 forms one or more infrared emitting features on a pattern layer. In some embodiments, forming the one or more infrared emitting features includes positioning the infrared emitting features in a predetermined pattern. For example, the infrared emitting features may be positioned on the pattern layer in a predetermined pattern such that the predetermined pattern corresponds to positions along the conductive path. In an embodiment, forming the one or more infrared emitting features includes positioning the infrared emitting features within a gap formed by metal trace points such that adjacent metal trace points are connected. In some embodiments, forming the one or more infrared emitting features includes forming an array of infrared light emitting diodes (LEDs).

Alternatively, block 1214 forms one or more reflective features on a pattern layer. In some embodiments, forming the reflective features includes positioning the reflective features over portions of the conductive path in a predetermined pattern. The reflective features reflect infrared light from the base layer, thereby emitting a predetermined infrared pattern having a temperature gradient.

In block 1016, the base layer and the pattern layer are coupled. A power source generates current within the conductive path. In an embodiment, the one or more infrared emitting features emit infrared light in a predetermined infrared pattern. In another embodiment, the reflective features block portions of the emitted infrared light emitted from the base layer and provides a predetermined pattern of infrared light. In a further embodiment, the base layer and/or the pattern layer may be replaced with a different base layers and/or pattern layers, respectively, to emit infrared light along different predetermined patterns.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Having described preferred embodiments of thermal tags for real-time activity monitoring and methods for fabricating the same (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A thermal tag for activity monitoring, comprising:
one or more heat point sources connected to a plurality of metal lines in the tag, the plurality of metal lines including metal trace points separated from adjacent metal trace points by a gap; and
one or more infrared emitting features positioned over the one or more heat point sources, wherein at least one infrared emitting feature is configured to emit a particular infrared pattern to indicate an associated with the infrared pattern particular activity.

2. The thermal tag of claim 1, wherein the one or more infrared emitting features includes at least one material selected from the group consisting of electrically conducting material and thermally conductive material.

3. The thermal tag of claim 2, wherein the at least one infrared emitting feature is positioned within the gap to connect respective adjacent metal trace points.

4. The thermal tag of claim 3, wherein the at least one infrared emitting features includes an infrared light emitting diode.

5. The thermal tag of claim 3, wherein the one or more metal trace points are selectively positioned in a predetermined pattern.

6. The thermal tag of claim 5, wherein the one or more infrared emitting features includes an array of infrared light emitting diodes.

7. The thermal tag of claim 1, wherein the one or more infrared emitting features includes thermally conductive patches positioned over respective heat point sources, the thermally conductive patches having a heat spreading element to emit a temperature gradient within the predetermined infrared pattern.

8. The thermal tag of claim 1, wherein portions of the plurality of metal lines are coated with a thin dielectric material.

9. A thermal tag for activity monitoring, comprising:
a plurality of metal lines to provide a conductive path, the plurality of metal lines being configured to emit infrared light and including metal trace points separated from adjacent metal trace points by a gap; and
one or more infrared reflective features positioned over portions of the conductive path, wherein at least one infrared reflective feature is configured to block portions of the infrared light to emit a particular infrared pattern to indicate a particular activity.

10. The thermal tag of claim 9, wherein the predetermined infrared pattern includes a temperature distribution pattern.

11. The thermal tag of claim 9, wherein the one or more infrared reflective features includes at least one reflective material.

12. The thermal tag of claim 9, wherein the metal lines provide a uniform heat gradient.

13. A method for fabricating a thermal tag for activity monitoring, comprising:
forming a plurality of metal lines and one or more heat point sources between adjacent metal lines such that the adjacent metal lines are connected, the forming the plurality of metal lines including printing metal trace points such that the metal trace points are separated from adjacent metal trace points by a gap; and
forming one or more infrared emitting features positioned over the one or more heat point sources, wherein at least one infrared emitting feature is configured to emit a particular infrared pattern to indicate an associated with the infrared pattern particular activity.

14. The method of claim 13, wherein forming the one or more metal trace points includes positioning the one or more metal trace points in a predetermined pattern.

15. The method of claim 13, wherein forming the one or more infrared emitting features includes forming thermally conductive patches positioned over respective heat point sources, the thermally conductive patches having a heat spreading element to emit a temperature gradient within the predetermined infrared pattern.

16. The method of claim 13, further comprising forming a thin dielectric material over portions of the plurality of metal lines.

* * * * *